United States Patent [19]

Vognsen et al.

[11] 4,442,215

[45] Apr. 10, 1984

[54] ELEMENT-RICH COMPOSITION

[75] Inventors: Anders M. Vognsen, Sollerod Slotsvej 17, DK-2840 Holte; Henrik Boisen, Virum, both of Denmark

[73] Assignee: Anders Marius Vognsen, Sollerod, Denmark

[21] Appl. No.: 310,075

[22] PCT Filed: Feb. 11, 1981

[86] PCT No.: PCT/DK81/00013

§ 371 Date: Oct. 12, 1981

§ 102(e) Date: Oct. 12, 1981

[87] PCT Pub. No.: WO81/02242

PCT Pub. Date: Aug. 20, 1981

[30] Foreign Application Priority Data

Feb. 11, 1980 [DK] Denmark ............................. 589/80

[51] Int. Cl.$^3$ ............................................. C07G 17/00
[52] U.S. Cl. .................................... 435/262; 426/583; 106/DIG. 1; 71/DIG. 2; 71/11
[58] Field of Search .......................... 71/1, 11, 6, 7, 31, 71/63, DIG. 2; 106/DIG. 1; 210/606; 426/583; 435/262, 267

[56] References Cited

U.S. PATENT DOCUMENTS 4,313,753  2/1982  Segawa et al. ............... 106/DIG. 1

FOREIGN PATENT DOCUMENTS 1026580  2/1978  Canada ................................... 71/7
1460044  12/1976  United Kingdom .

*Primary Examiner*—Ferris H. Lander

[57] ABSTRACT

A method for preparing an element-rich composition for use as supplement in biological or physiological systems, comprising subjecting fly ash to the influence of reactants capable of dissolving a plurality of the components of the fly ash into a biologically assimilable form selected from chelates, complexes and lactic acid salts and obtaining the biologically assimilable form of the fly ash, and an element-rich composition prepared according to this method, the use of said element-rich composition as source of elements for animal and human consumption and in processes in which one or more elements, including trace elements, are essential.

10 Claims, No Drawings

ELEMENT-RICH COMPOSITION

The present invention relates to a method for preparing an element-rich composition for use as supplement in biological and physiological systems.

The supplying of minerals to human beings and animals is desirable because the intensive utilization of the cultivated areas results in the soil being depleted. The plants growing on this soil become gradually poor in trace elements which are taken up by the plants, but which are not added by the fertilization. This depletion of the soil may result in a lack of certain minerals in the plants cultivated in the soil, and thereby also through the food chain, in the animals consuming the plants and in the human beings who partly consume the plants directly and partly consume the animals.

Thus, the usual process for the preparation of mineral compositions containing a large number of mineral salts comprises reacting each mineral, e.g. in the form of an oxide, with a suitable acid and, after isolation of the individual mineral salts, mixing them to form the end composition. This process is very time-consuming and costly.

Fly ash from power stations using, as fuel, hard coal in pulverized form, contains, like the fuel from which it has been formed, a very rich spectrum of elements, including a very high number of trace elements. Furthermore, the spectrum of elements present in the fuel and, hence, although modified by the combustion at about 1000° C., present in the fly ash, must necessarily reflect and be correlated with the spectrum of elements in the plants which, hundreds of millions of years before our time, constituted the main origin of the fossil fuel.

The terms "rich in elements" and "element-rich" are intended to designate a content of a large number of elements, and in particular, a broad spectrum of trace elements. The term "mineral" is intended to designate a material of inorganic origin containing a number of elements.

It is known that the supplying of elements and especially trace elements to human beings and animals may conveniently be performed in the form of mixtures of mineral compounds which are readily dissociable in the organism. It is especially suitable to administer compounds in which the anion is readily convertible in the organism, e.g. citrates, tartrates, ascorbates, lactates, acetates, propionates, gluconates, chlorides, sulphates, carbonates or phosphates.

It is known that many minerals are absorbed only as chelates or as complexes. Once chelated or complexed they may move into the intestinal cell. In the field of nutrition natural chelates and complexes such as chelates and complexes with amino acids and/or proteins and/or polypeptides play a major role in the mineral metabolism. The key to absorption is the substance with which the minerals are chelated or complexed.

According to a paper presented at International College of Applied Nutrition Los Angeles, Calif., Apr. 26, 1974, e.g. Rubin (Rubin, M., "Chelation and Iron Metabolism", Proc. AFMA Nutrition Council, November, 1967) has found that neither iron citrate nor iron fructose are as effective as some other iron chelates in placental diffusion of iron to the fetus.

According to the present invention, it is now possible to prepare an element-rich supplement composition in an extremely simple manner from very cheap waste products.

The present invention relates to a method for preparing an element-rich composition for use as supplement in biological and physiological systems, comprising subjecting fly ash as defined above to the influence of reactants capable of dissolving a plurality of the components of the fly ash into a biologically assimilable form selected from chelates, complexes and lactic acid salts and obtaining the biologically assimilable form of the fly ash, and an element-rich composition prepared according to this method, the use of said element-rich composition as source of elements for animal and human consumption and in processes in which one or more elements, including trace elements, are essential such as fermentation, and in biological processes.

In one aspect of the invention the fly ash is treated with lactic acid in an aqueous solution under conditions such that a plurality of the components of the fly ash become dissolved in the aqueous solution. The element-rich composition according to the invention may be obtained in liquid form by separation of the aqueous solution from the solids. The aqueous solution may be used per se, or it may be evaporated to yield a concentrated liquid or a dry product. The separation step may be performed by filtration, centrifugation or decanting.

In a further aspect of the invention fly ash is included in a fermentation liquor in which a lactic acid-producing bacterium is cultivated, and fly ash components in biologically assimilable form are obtained from the fermentation liquor.

Thus, in this embodiment of the invention, the reagents capable of dissolving a plurality of the components of the fly ash into a biologically assimilable form are present in the fermentation liquid in which the lactic acid-producing bacterium is cultivated. It is not known with certainty exactly how the dissolution of the fly ash components takes place in this case; it is likely, however, that the mechanism either comprises an initial solution of the fly ash components by lactic acid generated in situ, with a subsequent or simultaneous complex-forming or chelation with other components of the fermentation liquor, may be amino acid, peptides or proteins, or the mechanism may comprise an initial dissolution of the fly ash components in chelated or complex-bound form by components present in the fermentation liquor without the lactic acid playing any predominant role in the dissolution of the fly ash components.

The fermentation may be performed with a lactic acid-producing bacterium of the family Streptococcaceae or Lactobacillaceae, e.g. of the genus Streptococcus, Leuconostoc, Pediococcus or Lactobacillus. A preferred genus is Lactobaccillus, a preferred species is *Lactobacillus plantarum*, an especially preferred strain being Lactobacillus plantarum CH-1. It is preferred to perform the fermentation at an optimum temperature, preferably a temperature of about 30° C. or slightly above 30° C., which is the optimum fermentation temperature for this bacterium. The fermentation takes place in the presence of the usual sources of nitrogen, e.g. normal sources of vegetable, fish or animal protein origin, preferably milk protein.

For the cultivation of the lactic acid-producing bacterium any substrate comprising fermentable sugar such as whey or molasses may be used. The sugar substrate solution may contain from about $\frac{1}{2}\%$ of sugar dry matter to more than about 30% of sugar dry matter, the upper limit being determined by the conditions under which the microorganism used can grow. In order to render the polysaccharides more readily digestible by the bacterium, a di- or polysaccharide-degrading enzyme may be added. In addition to the fly ash and the sugar-containing substrate organic nitrogen compounds and nutritive salts necessary for the lactic acid fermentation may be added.

Thus, it will be understood, one embodiment of the present invention comprises using, as reagent to yield a dissolved form of the elements in the fly ash, lactic acid formed in situ during the reaction by fermentation of a sugar-containing substrate with a lactic acid-producing bacterium. In such a lactic acid fermentation in the presence of fly ash the lactic acid will, as it is formed, be reacted with the minerals, and as the lactic acid is thereby removed from the reaction mixture, it will not have a restraining influence on the further fermentation.

It is of advantage to use whey in the fermentation liquid in which the lactic acid-producing bacterium is cultivated as whey is a waste product which is produced in large amounts in the dairy industry. This waste product causes severe problems for the dairy industry as there are many restrictions on the disposal thereof for environmental reasons. Therefore, many attempts have been made to find a use for this product. Until now, the most common use has been as fodder additive for porkers.

According to a preferred aspect of the invention, whey retentate is used as the sugar-containing substrate. Whey retentate is the product formed when whey has been subjected to ultrafiltration. In this process, the whey is concentrated to a sugar content of up to 18%. The whey concentrate may be used as such, but it is preferred to add lactase in order to increase the conversion rate of lactose into monosaccharides (glucose and galactose) and nutritive ingredients, e.g. yeast extract.

Advantageously whey or whey retentate is used in diluted form, as the sugar concentration, and hence the osmotic pressure, is determinative for the growth of the bacteria.

In a preferred embodiment of the invention the fermentation liquid comprises whey retentate diluted with water in the ratio of 1:4–1:9, proteins, other suitable nutritive factors and fly ash. It is contemplated that successive addition of whey or whey retentate so that a constant sugar content of about 1–5%, e.g. 2–3%, is maintained in the fermentation liquor, will result in a maximum conversion into lactic acid and, hence, a maximum dissolution of the components of the fly ash.

According to a preferred aspect of the present invention a slurry containing fly ash and optionally desired further minerals, preferably in the form of oxides or carbonates, e.g. iron, manganese, zinc, cuprous and cobalto oxides or carbonates, is prepared in a whey retentate solution containing from about 3% of sugar dry matter to more than 25% of sugar dry matter, said solution being inoculated with a lactic acid bacterium, e.g. *Lactobacillus plantarum* or *Lactobacillus delbrueckii* (formerly called *Thermobacterium cereale*), and the fermentation is performed at about 30% C. with stirring.

In this reaction the lactic acid is formed simultaneously with the use thereof to yield lactates, and thus it is not necessary, as in the known art, to produce and isolate the lactic acid and the desired mineral ions separately and thereafter react them with each other.

According to a further aspect of the present invention the fly ash is treated with a reagent forming readily soluble mineral chelates with the minerals in the fly ash to yield chelated mineral mixtures, chelates being formed with minerals from crude fly ash and not, as it is known, with individual minerals. It is in this manner possible to prepare chelated minerals with the easily dissociable mineral compounds prepared according to the present invention.

A chelation may take place between the ions liberated in the solution and the amino acids originating from the proteins. It is contemplated that further chelation or complexing may be achieved by addition of amino acids, polypeptides and/or proteins to the liquid both. It is preferred to add further protein components to the whey retentate, and a preferred source of proteins is pasteurized non-fat dry milk (e.g. UHT-treated 9% NFDM).

Thus, an especially preferred embodiment of the invention relates to a process for the preparation of an element-rich composition in complexed or chelated form in which fly ash is treated with a liquid comprising whey retentate, a further source of proteins, e.g. milk and yeast extract, and a lactic acid-producing bacterium.

In such a combined broth, different buffer systems exist, i.e. proteins and salts. In the presence of fly ash, part of the lactic acid will, as it is formed, react with the minerals, and as the lactic acid is thereby partly removed from the reaction mixture, it will have a less restraining influence on the further fermentation.

When the cultivation is complete the slurry is filtered, decanted or centrifuged, and the liquid containing the minerals, optionally in complexed or chelated form, is isolated. This liquid may be used per se, or it may be absorbed on a carrier, optionally after evaporation, or it may be evaporated and, e.g., spray dried or freeze dried and used as a powder.

According to a further aspect of the invention, fly ash is subjected to the influence of an aqueous solution of an acid forming salts of the components of the fly ash, and the mixture formed is mixed with an agent forming soluble mineral complexes or chelates with the minerals in the fly ash. As acid may be used organic acids such as ascorbic acid, citric acid, tartaric acid, lactic acid, acetic acid, propionic acid or gluconic acid, or inorganic acids such as hydrochloric acid, sulphonic acid, carbonic acid or phosphoric acid. The reaction between the acid and the fly ash must be conducted under such conditions that a plurality of components in the fly ash are made available for the complex or chelate formation. The reaction time may be 0.5–24 hours, preferably 1–3 hours, and the acid treatment is preferably carried out with stirring.

Agents forming the complexes or chelates are as described above. Preferred agents are proteins of milk origin.

The agents forming soluble complexes or chelates may be used per se or in aqueous solution. The ratio between the fly ash in the mixture and the complex- or chelate-forming agent (calculated as complexing or chelating dry matter) is 1:1–100:1.

Prior to the bacterial growth, the pH in the mixture of fly ash and aqueous substrate will be alkaline, the pH being dependent on the amount of fly ash. As lactic acid-producing bacteria only grow slowly at alkaline pH values, it is assumed that better results with respect to the reaction time and, thus, the conversion rate within a pre-determined reaction time, may be achieved if an acid such as lactic acid is added in an amount which is sufficient for changing the pH to about 7.

In a preferred embodiment, fly ash is added, successively, to the fermentation broth concurrently with the acidulation caused by the growth of the bacteria. In this way, the alkaline reaction of the fly ash could be compensated for, and the maintaining of the pH at about 6-7 could result in a maximum bacterial growth. Such a successive addition of fly ash could be controlled, e.g. by a pH state.

Furthermore, better results with respect to the conversion of fly ash elements into an assimilable form may be achieved if the reaction period is prolonged. It is contemplated that a long reaction time, e.g. as used in the development in situ of lactic acid, will result in increased formation of the elements in a complex or chelated form.

After the treatment of fly ash with the fermentation liquor, in which the lactic acid-producing bacteria have been cultivated, or with a lactic acid solution, a solution of the desired minerals, optionally in complex or chelated form, has been obtained, and this solution is optionally neutralized by addition of a base, and the resulting liquid may be used per se or it may be mixed with a carrier, e.g. green fodder or grass meal, and the mixture may be dried.

The carrier used according to the process of the present invention may be a suitable fodder, a fodder additive or a pharmaceutically suitable carrier. For the administration to animals it is preferred to apply the obtained, optionally neutralized, solution on a carrier in the form of a fodder which is usually a component of the feed, but which is used in a minor amount, permitting a higher concentration of minerals on the carrier, thereby reducing the uncertainty in the dosing.

Suitable carriers may, e.g., be wheat bran or grass meal. Grass meal is dried and cut green fodder which is dried green crops such as clover, lucerne or grass. Grass meal may be used directly as fodder or optionally be preserved. The drying of grass meal is usually performed in a drum drier in which the hot exhaust gas from an oil burner is used as drying medium.

According to the present invention it is preferred to use grass meal, because it is cheaper than wheat bran which is a conventional carrier for mineral additives. Furthermore, grass meal has a constant composition and contains per se a broad spectrum of minerals.

When the carrier is grass meal it will often be unnecessary to dry the mixture if it is granulated as the heat developed thereby is sufficient for evaporating the water.

When green fodder, which typically contains 20-30% of dry matter, is used as carrier, the amount of mineral solution added may be reduced correspondingly, and the mineral solution is preferably applied immediately prior to the drying.

According to the present invention it is especially advantageous to neutralize with such a base in which the cation is a desired part of the mineral content. Thus for example potassium, sodium or calcium may in this way be added in the form of carbonates.

In a special aspect of the present invention the acidic mineral-containing solution obtained is neutralized by being added to a partly neutralized straw mass which has been treated with a base to improve of the fodder properties of the straw, and the resulting mass is dried, making up an improved fodder product.

The neutralized solution is applied on the carrier, preferably the grass meal, in an amount of 30-1% by weight of mineral solution on 70-99% by weight of carrier. In this way a product which is easy to handle and easy to dose is obtained.

When the fly ash has been treated by the process according to the present invention and the element-rich composition in liquid form has been applied on a carrier and thereafter dried, it has been fixed to the carrier.

The element-rich composition according to the invention may be used per se on the soil in fields or in green-houses.

The solution obtained by the process according to the present invention may, optionally after neutralization, be concentrated. The concentration may e.g. be performed by hyperfiltration or mainly partial evaporation. Concentration may be performed by simple evaporation, by evaporation under reduced pressure and optionally by spray drying.

A concentrate or an evaporation residue obtained may also be used as additive to fodders or to drinking water for animals. Concentration or evaporation results in element-rich compositions which are easier to transport if the compositions are to be mixed with a carrier on a site of use which is at a geographical distance from the site where the mineral composition was produced.

When the optionally neutralized solution has been applied on a carrier the resulting composition is dried if it is not used directly, and then it is advantageous to apply the solution on a fodder or fodder additive which must anyhow be dried during its preparation, and thus it is of course most advantageous to apply the prepared solution on the carrier by spraying before the drying.

The element-rich composition may be used in liquid form as a medium to be sprayed on to green fodder in order to ensilage it, optionally together with a lactic acid-producing bacterium, e.g. Lactobacillus plantarum CH-1. The bacterium is usually commercialized (by Chr. Hansen's Laboratorium A/S, Copenhagen, Denmark) as a freeze-dried product or a frozen product to be rehydrated and/or mixed with water before use. Instead of being mixed with water the bacterial product may be mixed with the liquid element-rich composition before use. A usual inoculum is $1 \times 10^{11} - 1 \times 10^{13}$ bacteria and this amount is intended for being mixed with 10 liters of water, part of which is the element-rich composition and thereafter sprayed on to 1 ton of green fodder for ensilage.

Tests indicate that a liquid element-rich composition prepared by the influence of lactic acid produced in situ by fermentation has an even more positive effect in bacterial processes than a liquid element-rich composition prepared by the influence of lactic acid (technical grade) although the pH values are very similar.

There are indications that the liquid element-rich compositions may substitute or improve the salts which are usually added to fermentation substrates.

It is contemplated that the element-rich composition in liquid form may be used as an additive in other biological processes, e.g. as additive to bacterial, yeast and mould cultures to be used in the food processing industry. As examples may be mentioned the use together with cultures developing lactic acid in various food products for the purpose of preservation or as a stimulating factor for specific cultivations.

Furthermore, it is contemplated that the element-rich composition in liquid form may be used per se as a liquid substrate in the preparation of extracts to be used in the preparation of other culture media. In the preparation of a complete medium the element-rich compositon in liquid form may be used as solvent for the nutritive agents. This solution is then dried to yield a powder which is rehydrated before use.

When the element-rich composition is evaporated to yield a dry product, this product may be used as additive in biological and physiological processes, e.g. in a microbial process and in human or animal use, respectively.

Tests have shown that the trouble in growing porkers, e.g. tail-biting, has been drastically reduced when the porkers have been given, as an additive to the fodder, an amount of the product prepared according to the invention. The product may be given as a liquid containing the optionally chelated product sprayed on green fodder in an amount of 1–20% of liquid on 99–80% of dried green fodder. This additive may be given to porkers in an amount of 0.1–2.5 g/feed unit (1 feed unit corresponds to the fodder value of 1 kg of barley).

When the element-rich composition prepared is to be administered as an additive to the fodder it is e.g. admixed with the fodder in amounts corresponding to 0.005–0.1, preferably 0.01–0.06, percent by weight of mineral substrate in the fodder ready for consumption by small animals, e.g. poultry. In case of medium size animals, e.g. porkers, the mineral composition is preferably incorporated in the fodder in an amount corresponding to 0.0015–0.025, preferably 0.0025–0.015, percent by weight of mineral substrate in the fodder ready for consumption, which fodder is typically given in an amount of about 2 kg/day/animal with a body weight of about 50 kg. For big animals, e.g. cows and horses, the mineral composition is preferably incorporated in the fodder in an amount corresponding to 0.003–0.06, especially 0.006–0.04, percent by weight of mineral substrate in the fodder which is typically given in an amount of about 14 kg/day/animal with a body weight of about 600 kg.

When the mineral composition is to be used in compositions which are to be administered to human beings the amount administered is suitably of a corresponding order in proportion to the body weight. For this use it is preferred that the composition administered is a tablet or powdery mineral additive composition of the same type as the mineral composition described in British Pat. No. 1,298,299, i.e. a composition comprising readily soluble salts of minerals such as sodium, potassium, calcium and magnesium, which has been enriched by addition of the trace element-rich composition according to the invention, e.g. by using, in the preparation of the tablet composition, the element-rich solution prepared according to the method of the present invention as granulating liquid. Another suitable administration form for human beings is a mineral water-like drink containing the minerals which have been made soluble.

Danish Patent Application No. 578/77 discloses a process for the preparation of an element-composition by contacting an element-rich material with water, optionally in the presence of an acid such as hydrochloric acid, sulphuric acid, acetic acid or ascorbic acid, to yield a dissolved form of the elements, optionally neutralizing and/or optionally applying it on or mixing it with a carrier and optionally drying it.

British Patent Specification No. 1,460,044 discloses the use of fly ash as additive to animal fodder, optionally together with compositions based on alkali and/or earth alkaline metal tartrates, citrates, lactates, glycerophosphates, gluconates and phosphates.

The compositions prepared according to the said process may be administered in any suitable form for oral administration.

In the process described above various mineral substrates having the common feature that they contain a large number of different minerals may be used, e.g. fly ash from power stations using, as fuel, hard coal in pulverized form, mineral-containing ores such as a copper ore, volcano ash, finely ground lava, finely ground dolomite or naturally occurring salts, and desired minerals not being present in the mineral substrate may optionally, e.g. in the form of oxides or carbonates, be added to the mineral substrate prior to the treatment with the reagent to yield readily soluble forms. In other words, the mineral substrate used need not directly contain all the desired minerals as such minerals which are by analysis shown to be missing may be added before the treatment to yield readily available forms.

U.S. Pat. No. 3,421,897 discloses a method for producing a food supplement which comprises a carrier and whey, having a usable iron component extracted from the carrier, which method comprises heating cultured whey until the whey is condensed by evaporation to the extent where it contains a major proportion of solids component, and only a minor proportion of liquid component and an increased lactic acid content, mixing the condensed whey with an iron-containing carrier, and without prior drying, curing the resulting mixture until sufficient iron is extracted from the carrier to provide a food supplement having an appreciable usable iron content extracted from said carrier. The resulting free-flowing particulate product contains up to 0.6% of soluble ferric iron.

German Auslegeschrift No. 2 034 692 discloses the preparation of an essential trace element composition by simply dissolving the trace element-containing material (e.g. $CuSO_4$, $FeSO_4$, $7H_2O$ or a water-soluble mixture of salts of trace elements) in whey. The whey may be concentrated whey, whey which has been partially de-sugarized, whey which has been exposed to partial protein-decomposition, and whey which has been exposed partly to de-sugarizing, partly to proteolytic decomposition. The said trace elements are, according to the German Auslegeschrift, able to form complexes, which results in a better physiological utility of the trace elements. Examples of trace element-containing materials are oxides, hydroxides and salt, water-soluble salts being preferred. The concentration of the trace element-rich material is 1–8 percent by weight, based upon lactose-free dry matter in the whey.

According to the known art, element-containing compositions comprising only a restricted number of elements or a plurality of elements in a less suitable form are prepared. According to the present invention compositions comprising a plurality of elements in biologically assimilable form are prepared in an extremely simple manner from very cheap waste products as starting materials.

The process according to the present invention is further illustrated by the below examples:

EXAMPLE 1

Fly ash was used directly as additive in a biological system. The added amount appears from Table I, in which the fly ash per se has been given fraction number 1.

Broth Y consisted of Broth X to which organic salts has been added in the following amounts:

|  | g/liter |
|---|---|
| Diammonium hydrogen citrate | 2.0 |
| Sodium acetate | 5.0 |

Broth Z

Broth Z consisted of Broth X to which inorganic salts had been added in the following amounts:

|  | g/liter |
|---|---|
| Di-potassium hydrogenphosphate | 2.0 |
| Magnesium sulphate | 0.1 |
| Manganese sulphate | 0.05 |

Broth Q

Broth Q consisted of Broth X to which both the organic salts mentioned under Broth Y and the inorganic salts mentioned under Broth Z had been added.

The broths were heated in an autoclave to 121° C. for ten minutes and cooled. Thereafter the broths were poured into 36 test tubes each containing 100 ml, and the fly ash fractions stated in Table I were added, and mixing was performed. 10 ml of broth were poured into test tubes, which were heated in an autoclave to 105° C. for 10 minutes.

After cooling, each of the test tubes was inoculated with about $3 \times 10^3$ bacteria, except sample No. 1 in each series of tests. The bacteria used were *Lactobacillus plantarum* CH-1, *Lactobacillus acidophilus* CH-2 and *Lactobacillus acidophilus* CH-5, respectively. The test tubes were incubated at 30° C. and 37° C., respectively, until growth appeared in one or more test tubes in each series of tests. Thereafter all the test tubes were cooled to 5° C. and pH measurements carried out.

As controls a corresponding number of test tubes were kept at 37° C. without inoculation, until all the inoculated test tubes had been incubated and cooled. The test tubes without bacteria were used as references in the evaluation of the growth of the bacteria.

The control values appear from Table II. The pH values for *Lactobacillus plantarum* CH-1, *Lactobacillus acidophilus* CH-2 and *Lactobacillus acidophilus* CH-5, respectively, appear from Tables III, IV and V, respectively. Tables III, IV and V also show the decrease in pH, which is an expression of the growth of the bacteria.

TABLE II

| Sample No. | Broth X | Broth Y | Broth Z | Broth Q |
|---|---|---|---|---|
| 1 | 6.22 | 5.69 | 6.40 | 6.08 |
| 2 | 6.23 | 5.69 | 6.40 | 6.08 |
| 3 | 6.23 | 5.73 | 6.44 | 6.10 |
| 4 | 6.60 | 5.87 | 6.58 | 6.25 |
| 5 | 6.22 | 5.73 | 6.43 | 6.04 |
| 6 | 6.30 | 5.55 | 6.50 | 6.10 |
| 7 | 6.25 | 5.71 | 6.45 | 6.06 |
| 8 | 6.44 | 5.81 | 6.49 | 6.07 |
| 9 | 5.97 | 5.64 | 6.35 | 5.99 |
| 10 | 5.40 | 5.50 | 5.62 | 5.72 |
| 11 | 6.10 | 5.68 | 6.40 | 6.01 |
| 12 | 6.04 | 5.68 | 6.37 | 6.02 |
| 13 | 5.97 | 5.65 | 6.30 | 5.98 |
| 14 | 5.56 | 5.46 | 5.78 | 5.75 |
| 15 | 6.14 | 5.69 | 6.43 | 6.02 |
| 16 | 6.04 | 5.69 | 6.40 | 6.01 |
| 17 | 6.12 | 5.68 | 6.42 | 5.99 |
| 18 | 6.08 | 5.68 | 6.34 | 5.98 |
| 19 | 6.10 | 5.68 | 6.40 | 6.02 |
| 20 | 6.13 | 5.68 | 6.40 | 6.03 |
| 21 | 6.16 | 5.68 | 6.42 | 6.03 |
| 22 | 6.28 | 5.76 | 6.45 | 6.06 |
| 23 | 6.13 | 5.70 | 6.42 | 6.08 |
| 24 | 6.16 | 5.72 | 6.42 | 6.02 |
| 25 | 6.08 | 5.67 | 6.40 | 6.01 |
| 26 | 5.97 | 5.63 | 6.27 | 5.94 |
| 27 | 6.12 | 5.69 | 6.40 | 6.01 |
| 28 | 5.94 | 5.66 | 6.35 | 5.93 |
| 29 | 6.12 | 5.68 | 6.43 | 6.01 |
| 30 | 6.15 | 5.70 | 6.38 | 6.02 |
| 31 | 6.08 | 5.70 | 6.40 | 6.03 |
| 32 | 6.12 | 5.67 | 6.37 | 6.00 |
| 33 | 6.00 | 5.67 | 6.39 | 5.98 |
| 34 | 5.68 | 5.58 | 6.26 | 5.90 |
| 35 | 6.03 | 5.69 | 6.43 | 6.00 |
| 36 | 6.03 | 5.68 | 6.39 | 5.98 |

When assessing the figures stated in Table III, IV and V the following should be noted:

Sample No. 1 is the control. Sample No. 2 is an inoculated control which is used as a reference for the assessment of sample Nos. 3–16, and sample Nos. 33–36 are references for the assessment of sample Nos. 17–32.

TABLE III

*Lactobacillus plantarum* CH-1

| Sample No. | Broth X pH | Broth X Decrease in pH | Broth Y pH | Broth Y Decrease in pH | Broth Z pH | Broth Z Decrease in pH | Broth Q pH | Broth Q Decrease in pH |
|---|---|---|---|---|---|---|---|---|
| 1 | 6.10 | 0.12 | 5.70 | 0.01 | 6.50 | −0.10 | 6.00 | 0.08 |
| 2 | 5.50 | 0.73 | 5.60 | 0.09 | 6.03 | 0.37 | 5.71 | 0.37 |
| 3 | 4.90 | 1.33 | 5.20 | 0.53 | 5.47 | 0.03 | 5.32 | 0.78 |
| 4 | 4.65 | 1.95 | 4.90 | 0.97 | 4.49 | 2.09 | 4.84 | 1.31 |
| 5 | 5.54 | 0.68 | 5.50 | 0.23 | 5.97 | 0.46 | 5.34 | 0.70 |
| 6 | 5.63 | 0.67 | 5.44 | 0.11 | 5.31 | 1.19 | 5.29 | 0.81 |
| 7 | 5.00 | 1.25 | 5.27 | 0.43 | 5.68 | 0.23 | 5.30 | 0.76 |
| 8 | 4.75 | 1.69 | 5.05 | 0.76 | 5.19 | 1.30 | 5.07 | 1.00 |
| 9 | 4.35 | 1.62 | 4.53 | 1.11 | 4.79 | 1.56 | 4.80 | 1.19 |
| 10 | 4.09 | 1.31 | 4.48 | 1.02 | 4.32 | 1.30 | 4.48 | 1.24 |
| 11 | 5.00 | 1.10 | 5.35 | 0.33 | 5.86 | 0.54 | 4.96 | 1.05 |
| 12 | 4.73 | 1.31 | 5.04 | 0.64 | 5.36 | 1.01 | 5.03 | 0.99 |
| 13 | 4.37 | 1.60 | 4.72 | 0.93 | 4.67 | 1.33 | 4.83 | 1.15 |
| 14 | 4.12 | 1.44 | 4.53 | 0.93 | 4.31 | 1.47 | 4.51 | 1.24 |
| 15 | 5.00 | 1.14 | 5.43 | 0.26 | 5.90 | 0.53 | 5.38 | 0.64 |
| 16 | 4.77 | 1.27 | 5.07 | 0.62 | 5.19 | 1.21 | 5.16 | 0.85 |
| 17 | 5.25 | 0.87 | 5.50 | 0.18 | 5.65 | 0.77 | 5.31 | 0.68 |
| 18 | 4.87 | 1.21 | 5.20 | 0.48 | 5.10 | 1.24 | 5.07 | 0.91 |
| 19 | 5.20 | 0.90 | 5.36 | 0.32 | 5.77 | 0.63 | 5.30 | 0.72 |
| 20 | 4.98 | 1.15 | 5.15 | 0.53 | 5.48 | 0.92 | 5.23 | 0.80 |
| 21 | 5.40 | 0.76 | 5.55 | 0.13 | 5.57 | 0.85 | 5.50 | 0.53 |
| 22 | 5.25 | 1.03 | 5.42 | 0.34 | 4.90 | 1.55 | 5.30 | 0.76 |
| 23 | 5.05 | 1.08 | 5.43 | 0.27 | 5.87 | 0.55 | 5.44 | 0.64 |
| 24 | 4.98 | 1.18 | 5.05 | 0.67 | 5.22 | 1.20 | 5.15 | 0.87 |
| 25 | 5.50 | 0.58 | 5.55 | 0.12 | 5.99 | 0.41 | 5.52 | 0.49 |
| 26 | 5.28 | 0.69 | 5.40 | 0.23 | 4.97 | 1.30 | 5.26 | 0.68 |
| 27 | 5.35 | 0.77 | 5.42 | 0.27 | 5.97 | 0.43 | 5.38 | 0.63 |
| 28 | 5.10 | 0.84 | 5.20 | 0.46 | 5.70 | 0.65 | 5.25 | 0.68 |
| 29 | 5.55 | 0.57 | 5.58 | 0.10 | 5.72 | 0.71 | 5.50 | 0.51 |
| 30 | 5.33 | 0.82 | 5.43 | 0.27 | 4.73 | 1.65 | 5.80 | 0.22 |
| 31 | 5.30 | 0.78 | 5.48 | 0.22 | 5.74 | 0.66 | 5.42 | 0.61 |
| 32 | 5.10 | 1.02 | 5.20 | 0.47 | 5.51 | 0.86 | 5.48 | 0.52 |
| 33 | 5.53 | 0.47 | 5.55 | 0.22 | 6.00 | 0.39 | 5.38 | 0.60 |
| 34 | 5.25 | 0.43 | 5.45 | 0.13 | 5.81 | 0.45 | 5.28 | 0.62 |
| 35 | 5.62 | 0.41 | 5.62 | 0.07 | 6.14 | 0.29 | 5.40 | 0.60 |
| 36 | 5.55 | 0.48 | 5.55 | 0.13 | 6.11 | 0.28 | 5.45 | 0.53 |

EXAMPLE 2

One part by weight of fly ash was added to two parts by weight of tap water with stirring. The slurry was left with stirring for 24 hours at 30° C. Thereafter part of the mixture was centrifuged (8000 g for 10 minutes) and the supernatant was decanted.

The liquid was subjected to sterile filtration ($0.45\mu$) to yield fraction 2.1.

The sediment from the centrifugation is fraction 2.2.

The added amounts of each of the fractions appear from Table I.

EXAMPLE 3

Example 2 was repeated, the pH value, however, being maintained at 4.8 in a pH state by addition of 80% lactic acid.

Liquid fraction 3.1 was obtained in the same manner as fraction 2.1.

Sediment fraction 3.2 was obtained in the same manner as fraction 2.2.

Part of the remaining slurry was adjusted to pH 6.5 by addition of 25% $NH_4OH$, and the liquid was left for 10 minutes, whereafter centrifugation and decanting was carried out as described in Example 2.

Liquid fraction 3.3 was obtained in the same manner as fraction 2.1.

Sediment fraction 3.4 was obtained in the same manner as fraction 2.2.

The added amounts of each of the fractions appear from Table I.

EXAMPLE 4

To 8 liters of whey retentate (about 22% dry matter) were added 5000 lactase units, 40 ml of yeast extract (about 12 g), 0.5 kg of fly ash and $8 \times 10^9$ bacteria (Lactobacillus plantarum CH-1). The mixture was incubated with stirring under inert gas at 30° C. until a pH of 5.0 was obtained. Part of the mixture was centrifuged and decanted as described in Example 2.

Liquid fraction 4.1 was obtained in the same manner as fraction 2.1. Sediment fraction 4.2 was obtained in the same manner as fraction 2.2.

The pH of the remaining part of the mixture was adjusted to 6.5 by addition of 25% $NH_4OH$. The mixture was centrifuged and decanted as described in Example 2.

Liquid fraction 4.3 was obtained in the same manner as fraction 2.1.

Sediment fraction 4.4 was obtained in the same manner as fraction 2.2.

The added amounts of each of the fractions appear from Table I.

EXAMPLE 5

Example 4 was repeated, except that 50% of the retentate was substituted by 9% UHT-treated skimmilk (NFDM; non-fat dry milk), and the fermentation was continued until pH 4.5.

Liquid fraction 5.1 was obtained in the same manner as fraction 4.1.

Sediment fraction 5.2 was obtained in the same manner as fraction 4.2.

Liquid fraction 5.3 was obtained in the same manner as fraction 4.3.

Sediment fraction 5.4 was obtained in the same manner as fraction 4.4.

EXAMPLE 6

Example 5 was repeated, except that no fly ash was used, and the acidification was performed by addition of 80% lactic acid until pH 4.8.

Liquid fraction 6.1 was obtained in the same manner as fraction 5.1.

Sediment fraction 6.2 was obtained in the same manner as fraction 5.2.

The added amounts of each of the fractions appear from Table I.

It should be noted that in Examples 1-3, the ratio between fly ash and liquid is 1:2 (by weight), whereas the ratio between fly ash and liquid in Examples 4 and 5 is 1:16 (by weight).

TABLE I

| Amount of added fly ash, filtrate or sediment prepared according to the Examples 1-6 | Sample No. | Fraction number: | Amount of broth |
|---|---|---|---|
| None | 1 | | 100 ml |
| None | 2 | | 100 ml |
| 0.05 g | 3 | 1 | 100 ml |
| 0.25 g | 4 | 1 | 100 ml |
| 0.5 ml | 5 | 2.1 | 100 ml |
| 2.5 ml | 6 | 2.1 | 100 ml |
| 0.05 g | 7 | 2.2 | 100 ml |
| 0.25 g | 8 | 2.2 | 100 ml |
| 0.5 ml | 9 | 3.1 | 100 ml |
| 2.5 ml | 10 | 3.1 | 100 ml |
| 0.05 g | 11 | 3.2 | 100 ml |
| 0.25 g | 12 | 3.2 | 100 ml |
| 0.5 ml | 13 | 3.3 | 100 ml |
| 2.5 ml | 14 | 3.3 | 100 ml |
| 0.05 g | 15 | 3.4 | 100 ml |
| 0.25 g | 16 | 3.4 | 100 ml |
| 0.5 ml | 17 | 4.1 | 100 ml |
| 2.5 ml | 18 | 4.1 | 100 ml |
| 0.05 g | 19 | 4.2 | 100 ml |
| 0.25 g | 20 | 4.2 | 100 ml |
| 0.5 ml | 21 | 4.3 | 100 ml |
| 2.5 ml | 22 | 4.3 | 100 ml |
| 0.05 g | 23 | 4.4 | 100 ml |
| 0.25 g | 24 | 4.4 | 100 ml |
| 0.5 ml | 25 | 5.1 | 100 ml |
| 2.5 ml | 26 | 5.1 | 100 ml |
| 0.05 g | 27 | 5.2 | 100 ml |
| 0.25 g | 28 | 5.2 | 100 ml |
| 0.5 ml | 29 | 5.3 | 100 ml |
| 2.5 ml | 30 | 5.3 | 100 ml |
| 0.05 g | 31 | 5.4 | 100 ml |
| 0.25 g | 32 | 5.4 | 100 ml |
| 0.5 ml | 33 | 6.1 | 100 ml |
| 2.5 ml | 34 | 6.1 | 100 ml |
| 0.05 g | 35 | 6.2 | 100 ml |
| 0.25 g | 36 | 6.2 | 100 ml |

The samples prepared as described in Examples 1-6 were subjected to culture testing with three bacteria of the genus Lactobacillus in 4 cultivation broths: Broth X, Broth Y, Broth Z, and Broth Q, respectively. The compositions of the broths were as follows:

| Broth X | g/liter distilled water |
|---|---|
| Universal peptone ("Bacto Peptone") | 10.0 |
| Meat extract ("Lab Lemco") | 5.0 |
| Yeast extract ("Difco") | 5.0 |
| D(+)Glucose | 20.0 |
| Polyoxyethylene sorbitane monooleate ("Tween" ® 80) | 1.0 |

Broth Y

TABLE IV

Lactobacillus acidophilus CH-2

| Sample No. | Broth X pH | Decrease in pH | Broth Y pH | Decrease in pH | Broth Z pH | Decrease in pH | Broth Q pH | Decrease in pH |
|---|---|---|---|---|---|---|---|---|
| 1 | 6.16 | 0.06 | 5.67 | 0.02 | 6.40 | 0.00 | 6.00 | 0.08 |
| 2 | 5.67 | 0.56 | 5.65 | 0.04 | 5.62 | 0.78 | 5.63 | 0.45 |
| 3 | 5.42 | 0.81 | 5.52 | 0.21 | 5.55 | 0.89 | 5.46 | 0.64 |
| 4 | 6.39 | 0.21 | 5.45 | 0.42 | 5.87 | 0.71 | 5.33 | 0.92 |
| 5 | 5.50 | 0.72 | 5.63 | 0.10 | 5.55 | 0.88 | 5.55 | 0.49 |
| 6 | 5.52 | 0.88 | 5.67 | −0.12 | 5.75 | 0.75 | 5.55 | 0.55 |
| 7 | 5.42 | 0.83 | 5.57 | 0.14 | 5.50 | 0.95 | 5.52 | 0.54 |
| 8 | 5.60 | 0.84 | 5.50 | 0.31 | 5.62 | 0.87 | 5.43 | 0.64 |
| 9 | 5.20 | 0.77 | 5.57 | 0.07 | 5.60 | 0.75 | 5.58 | 0.41 |
| 10 | 5.19 | 0.21 | 5.40 | 0.10 | 5.37 | 0.25 | 5.58 | 0.14 |
| 11 | 5.55 | 0.55 | 5.60 | 0.08 | 5.50 | 0.90 | 5.57 | 0.44 |
| 12 | 5.33 | 0.71 | 5.55 | 0.13 | 5.40 | 0.97 | 5.54 | 0.48 |
| 13 | 5.15 | 0.82 | 5.53 | 0.12 | 5.45 | 0.85 | 5.49 | 0.49 |
| 14 | 5.17 | 0.39 | 5.15 | 0.31 | 5.33 | 0.45 | 5.60 | 0.15 |
| 15 | 5.53 | 0.61 | 5.62 | 0.07 | 5.60 | 0.77 | 5.58 | 0.44 |
| 16 | 5.19 | 0.85 | 5.55 | 0.14 | 5.34 | 1.06 | 5.53 | 0.48 |
| 17 | 5.41 | 0.71 | 5.49 | 0.19 | 5.30 | 1.12 | 5.42 | 0.57 |
| 18 | 5.09 | 0.99 | 4.80 | 0.88 | 5.04 | 1.30 | 5.16 | 0.82 |
| 19 | 5.43 | 0.67 | 5.56 | 0.12 | 5.40 | 1.00 | 5.47 | 0.55 |
| 20 | 5.15 | 0.98 | 5.52 | 0.16 | 5.44 | 0.96 | 5.46 | 0.57 |
| 21 | 5.45 | 0.71 | 5.49 | 0.19 | 5.78 | 0.64 | 5.48 | 0.55 |
| 22 | 5.10 | 1.18 | 4.93 | 0.83 | 5.15 | 1.30 | 5.27 | 0.79 |
| 23 | 5.27 | 0.86 | 5.60 | 0.10 | 5.46 | 0.96 | 5.50 | 0.58 |
| 24 | 5.13 | 1.03 | 5.50 | 0.22 | 5.45 | 0.97 | 5.47 | 0.55 |
| 25 | 5.32 | 0.76 | 5.52 | 0.15 | 5.36 | 0.96 | 5.42 | 0.59 |
| 26 | 5.14 | 0.83 | 5.08 | 0.55 | 5.07 | 1.20 | 5.42 | 0.52 |
| 27 | 5.44 | 0.68 | 5.58 | 0.11 | 5.30 | 1.10 | 5.58 | 0.43 |
| 28 | 5.17 | 0.77 | 5.55 | 0.11 | 5.17 | 1.18 | 5.55 | 0.38 |
| 15 | 5.53 | 0.61 | 5.62 | 0.07 | 5.60 | 0.77 | 5.58 | 0.44 |
| 16 | 5.19 | 0.85 | 5.55 | 0.14 | 5.34 | 1.06 | 5.53 | 0.48 |
| 17 | 5.41 | 0.71 | 5.49 | 0.19 | 5.30 | 1.12 | 5.42 | 0.57 |
| 18 | 5.09 | 0.99 | 4.80 | 0.88 | 5.04 | 1.30 | 5.16 | 0.82 |
| 19 | 5.43 | 0.67 | 5.56 | 0.12 | 5.40 | 1.00 | 5.47 | 0.55 |
| 20 | 5.15 | 0.98 | 5.52 | 0.16 | 5.44 | 0.96 | 5.46 | 0.57 |
| 21 | 5.45 | 0.71 | 5.49 | 0.19 | 5.78 | 0.64 | 5.48 | 0.55 |
| 22 | 5.10 | 1.18 | 4.93 | 0.83 | 5.15 | 1.30 | 5.27 | 0.79 |
| 23 | 5.27 | 0.86 | 5.60 | 0.10 | 5.46 | 0.96 | 5.50 | 0.58 |
| 24 | 5.13 | 1.03 | 5.50 | 0.22 | 5.45 | 0.97 | 5.47 | 0.55 |
| 25 | 5.32 | 0.76 | 5.52 | 0.15 | 5.36 | 0.96 | 5.42 | 0.59 |
| 26 | 5.14 | 0.83 | 5.08 | 0.55 | 5.07 | 1.20 | 5.42 | 0.52 |
| 27 | 5.44 | 0.68 | 5.58 | 0.11 | 5.30 | 1.10 | 5.58 | 0.43 |
| 28 | 5.17 | 0.77 | 5.55 | 0.11 | 5.17 | 1.18 | 5.55 | 0.38 |
| 29 | 5.30 | 0.82 | 5.53 | 0.15 | 5.50 | 0.93 | 5.51 | 0.50 |
| 30 | 4.95 | 1.20 | 5.17 | 0.53 | 4.99 | 1.39 | 5.40 | 0.62 |
| 31 | 5.30 | 0.78 | 5.63 | 0.07 | 5.43 | 0.97 | 5.50 | 0.53 |
| 32 | 5.10 | 1.02 | 5.51 | 0.16 | 5.05 | 1.32 | 5.48 | 0.52 |
| 33 | 5.31 | 0.69 | 5.58 | 0.09 | 5.42 | 0.97 | 5.48 | 0.50 |
| 34 | 5.20 | 0.48 | 5.40 | 0.18 | 5.17 | 1.09 | 5.45 | 0.45 |
| 35 | 5.46 | 0.57 | 5.64 | 0.05 | 5.54 | 0.89 | 5.53 | 0.47 |
| 36 | 5.28 | 0.75 | 5.60 | 0.08 | 5.40 | 0.99 | 5.47 | 0.51 |

TABLE V

Lactobacillus acidophilus CH-5

| Sample No. | Broth X pH | Decrease in pH | Broth Y pH | Decrease in pH | Broth Z pH | Decrease in pH | Broth Q pH | Decrease in pH |
|---|---|---|---|---|---|---|---|---|
| 1 | 6.18 | 0.04 | 5.68 | 0.01 | 6.43 | −0.03 | 6.01 | 0.07 |
| 2 | 4.79 | 1.46 | 5.60 | 0.09 | 4.47 | 1.93 | 4.95 | 1.13 |
| 3 | 4.47 | 1.76 | 5.32 | 0.41 | 4.38 | 2.06 | 4.94 | 1.16 |
| 4 | 4.52 | 2.08 | 5.11 | 0.76 | 4.55 | 2.03 | 5.05 | 1.20 |
| 5 | 4.95 | 1.27 | 5.57 | 0.16 | 4.45 | 1.98 | 5.03 | 1.01 |
| 6 | 4.75 | 1.55 | 5.54 | 0.01 | 4.43 | 2.07 | 4.95 | 1.15 |
| 7 | 4.57 | 1.68 | 5.40 | 0.31 | 4.45 | 2.00 | 4.95 | 1.11 |
| 8 | 4.40 | 2.04 | 5.79 | 0.02 | 4.35 | 2.14 | 4.90 | 1.17 |
| 9 | 4.40 | 1.57 | 5.05 | 0.61 | 4.50 | 1.85 | 4.83 | 1.16 |
| 10 | 4.55 | 0.85 | 4.80 | 0.70 | 4.58 | 1.04 | 4.78 | 0.94 |
| 11 | 4.58 | 1.52 | 5.50 | 0.18 | 4.45 | 1.95 | 4.97 | 1.04 |
| 12 | 4.45 | 1.59 | 5.30 | 0.38 | 4.53 | 1.84 | 4.80 | 1.22 |
| 13 | 4.52 | 1.45 | 4.95 | 0.70 | 4.55 | 1.85 | 4.85 | 1.13 |
| 14 | 4.57 | 0.99 | 4.75 | 0.71 | 4.57 | 1.21 | 4.76 | 0.99 |
| 15 | 4.50 | 1.64 | 5.50 | 0.19 | 4.44 | 1.99 | 4.97 | 1.05 |
| 16 | 4.28 | 1.76 | 5.28 | 0.41 | 4.36 | 2.04 | 4.90 | 1.11 |
| 17 | 4.53 | 1.59 | 5.40 | 0.28 | 4.44 | 1.98 | 4.96 | 1.03 |
| 18 | 4.38 | 1.70 | 4.86 | 0.82 | 4.35 | 1.99 | 4.80 | 1.18 |
| 19 | 4.46 | 1.64 | 5.40 | 0.28 | 4.35 | 2.05 | 4.90 | 1.12 |
| 20 | 4.40 | 1.73 | 5.05 | 0.63 | 4.32 | 2.08 | 4.84 | 1.19 |
| 21 | 4.50 | 1.66 | 5.45 | 0.23 | 4.45 | 1.97 | 5.04 | 0.99 |
| 22 | 4.40 | 1.88 | 4.97 | 0.79 | 4.39 | 2.06 | 4.92 | 1.14 |
| 23 | 4.46 | 1.67 | 5.49 | 0.21 | 4.40 | 2.02 | 5.00 | 1.08 |
| 24 | 4.32 | 1.84 | 4.95 | 1.07 | 4.35 | 2.07 | 4.83 | 1.19 |
| 25 | 4.94 | 1.14 | 5.42 | 0.25 | 4.40 | 2.00 | 4.95 | 1.06 |
| 26 | 4.45 | 1.52 | 4.91 | 0.72 | 4.29 | 1.98 | 4.80 | 1.14 |
| 27 | 4.75 | 1.37 | 5.57 | 0.12 | 4.33 | 2.07 | 5.00 | 1.01 |
| 28 | 4.48 | 1.46 | 5.40 | 0.26 | 4.38 | 1.97 | 4.78 | 1.15 |
| 29 | 4.50 | 1.62 | 5.45 | 0.23 | 4.48 | 1.95 | 4.93 | 1.08 |
| 30 | 4.31 | 1.84 | 4.97 | 0.73 | 4.38 | 2.00 | 4.80 | 1.22 |
| 31 | 4.46 | 1.62 | 5.57 | 0.13 | 4.41 | 1.99 | 4.92 | 1.11 |
| 32 | 4.42 | 1.70 | 5.35 | 0.32 | 4.32 | 2.05 | 4.88 | 1.12 |
| 33 | 4.48 | 1.52 | 5.53 | 0.14 | 4.37 | 2.02 | 4.92 | 1.06 |
| 34 | 4.35 | 1.33 | 5.29 | 0.29 | 4.35 | 1.91 | 4.78 | 1.12 |
| 35 | 4.58 | 1.45 | 5.58 | 0.11 | 4.52 | 1.91 | 4.92 | 1.08 |
| 36 | 4.60 | 1.43 | 5.55 | 0.13 | 4.45 | 1.94 | 4.94 | 1.04 |

Although the starting pH values (the reference values) are not identical, it is clearly shown in these columns when an effect is provable, doubtful or lacking. Tables III, IV and V may be summarized in Table VI:

TABLE VI

| | Broth X Samples | | Broth Y Samples | | Broth Z Samples | | Broth Q Samples | |
|---|---|---|---|---|---|---|---|---|
| | 3–16 | 17–32 | 3–16 | 17–32 | 3–16 | 17–32 | 3–16 | 17–32 |
| L.p. CH-1 | + | + | + | + | + | + | + | +/− |
| L a. CH-2 | +/− | + | +/− | + | ? | +/? | ? | + |
| L.a. CH-5 | +/− | + | +/− | + | − | − | − | − |

In the above table "+" indicates a positive effect, "+/−" indicates a variable, but mainly positive effect, "−" indicates absence of proved positive effect, and "?" indicates a variable effect.

Thus, the effect of adding the element composition is shown to be positive for all of the fractions of *Lactobacillus plantarum* CH-1.

With respect to *Lactobacillus acidophilus* CH-2, the effects of tests 1–3 are variable and doubtful, whereas the effects of tests 4–5 are substantially positive.

With respect to *Lactobacillus acidophilus* CH-5, the effects of adding the fractions prepared according to Examples 1–3 are variable in tests carried out in Broths X and Y, whereas the effects of adding the fractions prepared according to Examples 4–5 in Broths X and Y are positive. The effects of adding the fractions prepared according to Examples 1–3 and 4–5 are not positive. These results indicate that the addition of fly ash is advantageous in broths to which no inorganic salts have been added.

From Table VI appears that the addition of the fractions prepared according to Examples 4 and 5 (Samples 17–32) seems to be as good as or better than the addition of the fractions prepared according to Examples 1–3, in view of the fact that the amounts of fly ash in the starting material was only 1:8 in Examples 4 and 5 as compared to Examples 2 and 3.

It appears from Tables III–V that the addition of each fraction at the highest level results in the largest pH decrease and the lowest pH.

Hence, it is contemplated that if the ratios between fly ash and liquid in Examples 2–5 has been identical, an even better result as expressed in pH decrease in the resulting broth would have been obtained for samples 17–32 (corresponding to Examples 4 and 5). This assumption has been motivated by the fact that ash determinations in liquids obtained as described in Example 5 (Fraction 5:1) with the provision that the amounts of fly ash were 400 g and 1110 g, respectively, have shown 1.92% and 2.49%, respectively.

EXAMPLE 7

Comparative tests were carried out with *Lactobacillus plantarum* CH-1 without fly ash, with the same bacterium with added fly ash and with *Lactobacillus delbrueckii* with added fly ash.

The substrate consisted of: 1500 ml of 9% NFDM (non-fat dry milk), 1500 ml of whey retentate, 1875 lactase units and 15 ml of yeast extract and, in the cases where fly ash was added, 150 g of fly ash and in these substrates, the pH was adjusted to below 7 by addition of techncal lactic acid after 30 minutes. The pH values were recorded 1 hour, 13 hours and 24 hours after the initiation of the test, and the titrable acidity (titer) (ml 0.1 N NAOH/100 ml sample) was determined after 1 hour, 13 hours and 24 hours.

The results are summarized in Table VII below:

TABLE VII

|  | Lactobacillus plantarum CH-1 without fly ash | | Lactobacillus plantarum CH-1 with fly ash | | Lactobacillus delbrueckii with fly ash | |
| --- | --- | --- | --- | --- | --- | --- |
|  | titer | pH | titer | pH | titer | pH |
| 1 hour | 37 | 6.21 | 19 | 6.80 | 14 | 7.05 |
| 13 hours | 44 | 5.92 | 46 | 5.83 | 44 | 5.90 |
| 24 hours | 77 | 4.78 | 113 | 4.45 | 87 | 4.95 |

From Table VII appears that the addition of fly ash enhances the acid production, especially when *Lactobacillus plantarum* CH-1 is used, and that *Lactobacillus delbrueckii*, which is known to be growing very slowly, even in milk enriched with yeast extract, yields a considerable amount of acid when cultured as described above.

EXAMPLE 8

For the preparation of a mineral-containing composition 18 kg of fly ash, potassium iodide, iron, manganese, zinc, cuprous and cabalto oxide are added to a reaction flash containing 20 liters of technical acetic acid, and the mixture is stirred for 24 hours at 40° C., whereafter the liquid is decanted. The sediment containing unreacted clay and silicon compounds and sparingly soluble heavy metal compounds may, if desired, be used as a soil-improving agent.

The mineral-containing liquid is neutralized with a mixture of calcium, sodium and potassium carbonate, and magnesium phosphate is added, whereafter the liquid is mixed with grass meal in the ratio of 10% of liquid to 90% of carrier, and the mixture is dried with hot air in a commercial drum drier.

In this way a fodder mixture is prepared which comprises readily available mineral acetates and from which undesired heavy metals have been removed.

EXAMPLE 9

The process described in Example 8 is repeated, but instead of acetic acid hydrochloric acid of the same concentration as in the stomach (0.5%) is used. The reaction is performed at 35° C. for 24 hours. The mineral salts prepared by this process are readily soluble in stomach juice and considerably more readily available than the untreated compounds.

EXAMPLE 10

10 liters of molasses solution containing 12% of sugar dry matter, nutritive salts and organic nitrogen compounds are inoculated with a lactic acid bacteria culture of *Thermobacterium cereale*. Simultaneously, 0.9 kg of fly ash is added.

The fermentation is performed with stirring at 52° C., i.e. 5–6° C. above the optimum temperature for the bacteria, in order to avoid development of e.g. butyric acid bacteria cultures, which would convert the sugar in the molasses into butyric acid. The lactic acid formed reacts with the minerals and as the acid production increases the pH value is adjusted to about 5 by addition of potassium, sodium and calcium carbonate. At the end of the reaction the liquid is decanted and magnesium phosphate is added to the mineral lactate-containing liquid and mixed with grass meal in a ratio of 10% of liquid to 90% of grass meal.

In this process, a mineral product is obtained in which all of the minerals are readily reactive.

EXAMPLE 11

Chelation

To form a suitable, readily available mineral product 0.18 kg of fly ash, 0.21 kg of calcium carbonate, 1.07 kg of potassium carbonate, and 0.05 kg of magnesium carbonate and 4.50 kg of ethylene diamine tetraacetic acid are mixed in 120 liters of water and left with stirring overnight. This mixture in which the minerals are more readily available than the untreated minerals is mixed with 280 kg of grass meal and dried as described in Example 8.

EXAMPLE 12

An element-rich composition was prepared by adding 80 g of fly ash to 1 liter of whey retentate (22% dry matter) inoculated with *Lactobacillus delbrueckii*. The mixture was left with stirring for 22 hours at 48° C. The slurry was filtered through a filter cloth, and the liquid was poured over grass meal in an amount of 100 ml of liquid on 1 kg of grass meal.

This element-rich grass meal was mixed with the normal fodder for porkers in an amount of 1.5 g per feed unit (∼1 kg of barley).

698 porkers were fattened with the fodder prepared as described above and thereafter slaughtered.

During the fattening period the tail-biting decreased drastically compared with porkers fattened with normal foddder without the element-rich supplement.

When the porkers were ready for slaughtering, their feed consumption has been 2.92 feed unit per kg weight increase.

EXAMPLE 13

1.25 kg of fly ash were treated as described in Example 2 with 8 liters of water, the pH being maintained at 4.8 in a pH state by addition of 80% lactic acid. The mixture was left with stirring for 24 hours at 30° C. The whole mixture was transferred into 4 liters of whey (22% dry matter) plus 4 liters of 9% NFDM and was stirred for 6 hours at 30° C. The slurry was filtered and the liquid was used as described in Example 12.

EXAMPLE 14

4 liters of whey retentate and 4 liters of milk (9% NFDM) as described in Example 5 plus 0.5 kg of fly ash were stirred, and the pH was maintained at 4.8 with lactic acid (80%; technical grade) for 18 hours by means of a pH state. The mixture in which the minerals are readily available was decanted and the liquid was mixed with grass meal in ratio of 12% of liquid to 88% of grass meal. The product was used as an additive in animal feed.

I claim:

1. A method for preparing an element-rich composition for use in biological and physiological systems in complexed or chelated form comprising subjecting fly ash from power stations to the influence of acids capable of converting a plurality of the components into a salt form, and reacting the salts with an agent forming complexes or chelates with the minerals in the fly ash.

2. An element-rich composition comprising a plurality of fly ash components in a biological assimilable form selected from the group consisting of chelates, complexes and lactic acid salts.

3. A composition as claimed in claim 2 in liquid form.

4. A composition as claimed in claim 3 in concentrated form.

5. A method for preparing an element-rich composition for use in biological and physiological systems, comprising fermenting lactic acid producing bacteria in an aqueous fermentation medium containing fly ash, converting a plurality of the components of the fly ash into a biologically assimilable form and recovering the converted biologically assimilable mineral containing liquid after the completion of said fermentation.

6. The method of claim 5 in which said medium also contains whey retentate.

7. The method of claim 5 in which said medium also contains a protein source.

8. The method of claim 5 in which said medium also contains milk powder.

9. The mineral containing liquid produced by the method of claim 5.

10. The method of claim 5 in which as a further step said liquid after recovery is added to a fermentation medium.

* * * * *